(12) United States Patent
Shattuck et al.

(10) Patent No.: US 6,387,088 B1
(45) Date of Patent: May 14, 2002

(54) PHOTOIONIZATION ENABLED ELECTROCHEMICAL MATERIAL REMOVAL TECHNIQUES FOR USE IN BIOMEDICAL FIELDS

(76) Inventors: John H. Shattuck, 14 Vistazo West, Tiburon, CA (US) 94020; Bruno Strul, 485 Cervantes Rd., Portola Valley, CA (US) 94028

(*) Notice: Subject to any disclaimer, the term of this patent is extended or adjusted under 35 U.S.C. 154(b) by 0 days.

(21) Appl. No.: 09/439,737

(22) Filed: Nov. 15, 1999

Related U.S. Application Data
(60) Provisional application No. 60/141,674, filed on Jun. 30, 1999.

(51) Int. Cl.[7] .............................................. A61B 18/18
(52) U.S. Cl. ............................ 606/2; 606/10; 606/11; 606/13; 606/14; 606/41; 607/98; 128/898
(58) Field of Search .............................. 606/2, 3, 4, 5, 606/6, 7, 8, 9, 10, 11, 12, 13, 14, 15, 16, 32, 41; 604/23, 26; 216/65, 67; 607/98, 100, 101, 103; 128/898

(56) References Cited

U.S. PATENT DOCUMENTS 4,901,720 A * 2/1990 Bertrand ...................... 606/40
5,720,894 A * 2/1998 Neev et al. .................... 206/65

* cited by examiner

*Primary Examiner*—Linda C. M. Dvorak
*Assistant Examiner*—R. Kearney
(74) *Attorney, Agent, or Firm*—James F. Hann; Haynes, Beffel & Wolfeld LLP

(57) ABSTRACT

A method for controlled removal of surface tissue layer portions with a non-contact energy delivery modality that applies electrical energy to the targeted tissue surface to cause electrochemical ablation. The system provides (i) a UV energy source for irradiating a beam path through a selected neutral gas environment overlying the targeted tissue thereby creating an ionized gas volume (i.e., a conductive non-equilibrium plasma), and (ii) an electrical source for creating an intense electrical field in the ionized gas volume to thereby apply energy to the targeted surface layer to cause volatilization and removal of the surface layer in a plasma-mediated ablation. The ultrafast plasma creation events are repeated at a high repetition rate to ablate surface layer portions in a controlled manner. Each ultrafast plasma creation event is of such a high intensity and such a brief duration that thermal energy is not transferred to the tissue thus preventing collateral thermal damage to regions adjacent to the targeted site.

11 Claims, 17 Drawing Sheets

US 6,387,088 B1

PHOTOIONIZATION ENABLED ELECTROCHEMICAL MATERIAL REMOVAL TECHNIQUES FOR USE IN BIOMEDICAL FIELDS

CROSS-REFERENCE TO RELATED APPLICATIONS

This application claims priority from U.S. Provisional Patent Application Ser. No. 60/141,674 filed Jun. 30, 1999. This application is directly related to U.S. patent applications Ser. No. 09/317,768 filed May 24, 1999 titled Photoionized Gas Enabled Electrical Discharge Techniques for Plasma-Mediated Cold Tissue Ablation, and Ser. No. 09/049,711 filed Mar. 27, 1998 U.S. Pat. No. 6,053,404 titled Ionothermal Delivery System and Technique for Medical Procedures both of which are incorporated herein by this reference.

This application also is related to the following co-pending U.S. patent applications or Provisional U.S. Patent Applications, all of which are incorporated herein by reference: Ser. No. 20/126,778 filed Mar. 29, 1999 titled Electrospallation Tissue Decomposition Devices and Methods for Use in Image-Controlled Tumor Decomposition; Ser. No. 09/181,906 filed Oct. 28, 1998 U.S. Pat. No. 6,210,404 titled Microjoule Electrical Discharge Catheter for Thrombolysis In Stroke Patients; Ser. No. 20/156,026 filed Oct. 28, 1998 titled Micro-Catheter for Combination Acoustic-Pharmacologic Thrombolysis In Stroke Patients; Ser. No. 20/156,025 filed Oct. 28, 1998 titled Micro-Catheter for Electroacoustic and Photoacoustic Thrombolysis In Stroke Patients; and Ser. No. 20/156,025 filed Dec. 31, 1998 titled Micro-Electrical Discharge Devices and Methods for Use in Cardiovascular and Ophthalmic Procedures.

BACKGROUND OF THE INVENTION

1. Field of the Invention

The invention is conceptually related to co-pending Ser. No. 09/049,711 (Ionothermal Delivery System and Technique for Medical Procedures) in which an initial photonic-media interaction is used to create a photoconductive effect in media (e.g., tissue) to thereafter enable, enhance or focus the application of electrical energy to structure within a patient's body. More particularly, this invention relates to a novel method for non-contact application of intense electrical energy to a tissue surface for selectively removing thin surface layers without collateral thermal damage. The instrument of the invention utilizes (i) a UV light source to irradiate and thereby photoionize a path through a selected gas environment overlying the targeted tissue, and (ii) a high-energy electrical source for creating an electrical field in the ionized gas to thereby apply an intense electrical energy pulse to volatilize macrmolecules of the surface to cause a plasma-mediated removal of thin layers without transfer of thermal energy.

2. Description of the Related Art

Various energy delivery sources have been investigated for surgical tissue ablation or removal, including radiofrequency (Rf) current flow within tissue, high intensity focused ultrasound (HIFU) interactions in tissue and microwave energy absorption in tissue. In general, at high intensities, the above listed energy sources generate thermal effects that can vaporize tissue as the means of tissue ablation or removal. In other words, the energy sources elevate the temperature of water in intra –and extracellular spaces to above 100° C. thereby explosively vaporizing water to damage or destroy the tissue The drawback to such purely thermally-mediated ablations is significant collateral damage to tissue volumes adjacent to the targeted site. While in many surgical fields, the above-described collateral thermal damage may be acceptable, in fields such as neurology, interventional cardiology and ophthalmology, there is a need to prevent, or limit, any such collateral damage. These energy sources also have the disadvantage of typically requiring contact between the working end of the instrument and the tissue targeted for ablation.

Various laser systems also have been developed for tissue ablation or removal. The conventional long-pulse laser systems outside the UV range, wherein long-pulse is defined as a system operating in a range of 10's of nanoseconds to microseconds in pulse duration, have been found to be inefficient in volumetric tissue removal without causing extensive collateral damage. In a the conventional long-pulse laser system (e.g., Nd:YAG, Er:YAG, IR lasers), the photonic energy delivered to a targeted site does not directly disrupt the molecular integrity of surface layers of the site, but rather the energy is transferred into surrounding tissue volumes as photothermal energy, or photomechanical energy. These collateral effects propagate through surrounding tissues as heat, and perhaps mechanical shock waves, which manifest themselves as undesirable collateral damage. More specifically, the generally accepted model of volumetric ablation or removal with lasers having a pulse longer than tens or hundreds of picoseconds is described as follows: The energy absorption is chromophore dependent (and/or scattering dependent), and the energy transfer involves the heating of conduction band electrons by the incident beam of coherent photons which is followed by transfer of thermal energy to the structure's lattice. Ablation or damage occurs by conventional heat disposition resulting in vaporization, melting, or fracture of the structure. The rate of volumetric structure removal depends on thermal conduction through the structure lattice and its thermodynamic properties (heat capacity, heat of vaporization, heat of fusion, etc.). Thus, the minimum energy requirements to cause an ablation effect in the structure's properties may be defined by a threshold of incident laser energy per unit of structure volume at the target site, which threshold is directly dependent on pulse duration. It has been found that ablation thresholds generally require relatively long pulse durations, which in turn are the source of undesirable collateral photothermal or photomechanical damage.

In certain tissue ablation fields (e.g., thrombus ablation in cardiology; corneal ablation in ophthalmology), excimer lasers have been developed that emit high intensity pulses of ultraviolet (UV) light, typically with pulse duration in the 1 ns to 100 ns range. The short wavelengths, as well as sequenced nanosecond pulse regimes, define a substantially non-thermal form of tissue ablation sometimes termed photodecomposition. Such ablation with UV irradiation occurs since biological tissues exhibit strong absorption characteristics in the UV region of the electromagnetic spectrum (e.g., at c. 1.93 $\mu$m). Short wavelength UV photons are highly energetic and when radiated onto biological tissue can break the chemical bonds in molecules of the surface layer. Thus, a UV excimer laser can vaporize a surface tissue layer with minimal thermal energy being transferred to underlying tissue volumes. Tissue ablation with UV irradiation can be controlled depth-wise by varying the number of pulses of ns energy delivery, since each pulse only penetrates to a depth of about 0.25 $\mu$m to 1.0 $\mu$m per pulse. The objectives of UV laser-tissue ablation include the uniform application of energy to a tissue surface as shown in FIG. 1A. Such an even energy application, if applied in a series pulses, could result in the hypothetical ablation shown in FIG. 1B. In fact, the idealized ablation characteristics shown in FIGS. 1A–1B may not achievable with a UV laser. FIGS. 2A–2B represent uneven energy densities over a surface layer (see FIG. 2A) and the resultant uneven ablation (see FIG. 2B) that may be characteristic of certain UV laser ablations. A potentially significant disadvantage of UV laser ablation is the type of uneven ablation surfaces (as hypothetically represented in FIGS. 2A–2B). Such uneven ablations are highly undesirable for some biomedical applications (e.g., corneal shaping in ophthalmology).

A primary objective underlying the present invention is the development of technology for creating smooth ablations at a microscopic level, while at the same time providing for bulk removal. For this reason, it is useful to explain why, it is believed, that UV ablations may result non-smooth ablation surfaces as represented in the hypothetical ablations of FIGS. 2A–2B. FIGS. 3A–3F are graphic representations of a prior art UV ablation event in an extended sequence, although the ablation event or events actually occur within a period of 10's to 100's of ns (nanoseconds). FIG. 3A is an illustration of a targeted tissue surface with a UV laser above the tissue. FIG. 3B is a sectional view showing the surface layer within an initial ns interval of UV laser irradiation of the tissue surface. Next, FIG. 3C depicts the surface layer several ns or 10's of ns later when an ablation plume or ejecta E (plasma) has been ejected from the tissue surface. It is believed that this ejecta E or plasma absorbs substantially all UV laser energy thereafter still radiating. In other words, the beam's energy will be substantially blocked from reaching the tissue surface and the actual UV ablation will be terminated or will be randomly spotty. FIG. 3D thus depicts the ablation created after termination of UV energy delivery in this hypothetical situation. The resultant uneven energy application is potentially further aggravated by secondary effects of the ablation plume (ejecta) which secondarily transfer heat randomly to regions indicated at R outside the exact targeted site. Finally, FIGS. 3E–3F show the effects that may occur from multiple additional pulses of energy delivery making the ablation yet more uneven. It is an objective of the present invention to deliver energy to a tissue surface to overcome the disadvantages represented in a hypothetical ablation of FIGS. 3A–3F.

Besides the potential for uneven material removal characteristics in UV laser delivery, there are other disadvantages which may limit the applicability of UV lasers for ablations in biomedical fields. First, the desired lack of collateral damage in UV ablation is not always possible. It is accepted that a single pulse of UV photonic energy irradiating a tissue surface will not cause collateral damage. However, when the UV pulse repetition rate exceeds about 5 Hz, considerable photothermal collateral damage (as well as photomechanical collateral damage) has been observed. Thus, UV ablation results in low volumetric removals of tissue surfaces per unit of time, which cannot be accelerated since UV energy is absorbed at a very shallow depth, and such absorption depth cannot be varied. Also, while UV photons carry sufficient energy to directly break chemical bonds in surface molecules of tissue, some UV wavelengths also may be sufficiently energetic to promote mutagenic effects thus elevating concerns about the long-term health and health of the clinician and the patient.

What is needed is a method for selective decomposition or removal of targeted surface layer portions on structure of a patient's body: (i) that is performed in a non-contact manner (ii) that can be activated in a controlled mode to ratably remove thin layers of tissue to allow selective layer removal; (iii) that results in a smooth and even ablation; and (iv) that does not rely on linear absorption characteristics in tissue, and (v) that does not rely on thermal vaporization effects in tissue and the mechanism of bulk removal.

SUMMARY AND OBJECTS OF THE INVENTION

The principal objective of the present invention is to provide ultrafast pulsed applications of energy to a thin surface layer of body tissue to create a plasma-mediated ablation process, alternatively called herein a volumetric bulk removal process. The invention discloses the application of energy from an intense electrical field that interfaces with a targeted site on the tissue surface. By controlling the duration of pulses of energy application—and the repetition rate—in relation to the thermal relaxation time of the targeted surface of the tissue, it is postulated that the disclosed plasma-mediated tissue removal method will be a substantially cold process, i.e., there will be no substantial collateral thermal damage to tissue.

Each ultrafast pulse, or burst, of energy application in the disclosed ablation process is enabled by a sequence of distinct plasma formation processes to achieve the operational objectives of the invention. Each plasma creation event is separated by a controlled plasma decay interval. In an initial portion of this sequential process, photoionizaton of a beam path in a selected gas environment overlying the targeted site is created to allow subsequent electrical potential therein. In a second portion of the process, an intense electrical field is created in the photoionized and conductive plasma of the beam path that extends to the targeted site thus causing volatilization of macromolecules of the targeted surface layers to remove layer portions. To define the uses of such plasmas herein, it is useful to provide the following background. A plasma is a quasineutral (partly ionized) gas having a significant proportion of charged particles relative to neutral particles which may, in an equilibrium state, exhibit collective behavior. Of interest to this invention are non-equilibrium or highly dynamic microplasmas formed in a beam path that allows for non-contact electrical energy transfer to, or deposition of energy on, a thin surface layer of tissue to remove (ablate) material without transfer of thermal energy. In the lexicon of physicists, a plasma may be defined simply as an ionized gas, to distinguish it from ordinary or neutral gas. In a neutral gas, each gas atom carries the same number of negatively charged electrons orbiting its nucleus as there are positively charged protons in that nucleus. While a neutral gas may carry the potential of substantial chemical activity together with dynamic effects (e.g., fluid turbulence), such a neutral gas exhibits little or no response to electric and magnetic fields—and such neutral gases are unable to conduct electrical potential therethrough. A neutral gas environment, however, can be excited or energized to the plasma state when a sufficient proportion of its atoms become ionized by losing one or more electrons. Ionization can occur as a result of a number of processes, such as (i) a neutral gas becoming so hot as to cause the atoms to collide and jar loose electrons, (ii) a neutral gas being subjected to a high intensity light source that strikes the atoms with energetic photons that displace electrons from their orbits (photoionization), and (iii) a neutral gas being subjected to electric fields that are strong enough to strip away electrons from the atoms (field ionization).

The photoionized gas in the beam path as proposed herein consists of an accumulation of interpenetrating and interacting freely roaming charges (both negative and positive). This gas state can shifted from neutral to ionized by the means disclosed herein, it is believed, within the range of 10's of femtoseconds to 100's of picoseconds. For purposes of this disclosure, the initial plasma (photoionized gas) volume is formed by irradiating a captured neutral gas volume with an electromagnetic energy pulse having a wavelength ($\lambda$) ranging between about 150 nm to 265 nm (or more broadly, within the UV spectrum defined as $\lambda$ from about 10 nm to 300 nm; or, frequency range of about $1.0 \times 10^{15}$ Hz to $6.0 \times 10^{16}$ Hz). Thereafter, an intense application of energy is applied by to targeted surface layer by creating an ultrafast high-intensity electrical discharge within the ionized gas beam path that interfaces with the surface layer to cause an electrochemical volatilization of molecules of the surface layer, i.e., a plasma-mediated ablation. Each high intensity burst of electrical energy forms a critical density plasma at the surface layer thus removing bulk surface material that is ionized. According to this plasma-mediated form of electrochemical material removal, each energy pulse applied to the surface layer when above a certain threshold level is channeled into to the formation of ejecta (gas plume and tissue detritus) by the volatilization or decomposition of macromolecules of the surface layer. The plasma, or microplasma, decays rapidly as ejecta and the resulting plasma transfer heat and energy away from the surface layer (and also releases energy in the form of radiative emissions). It is postulated that such energy applications to the surface layer (dependent on ionization proportion of neutral gas and intensity of the electrical field), can be modeled to provide selective volumetric removal of material per discrete pulse of energy. In sum, a controllable process for selective volumetric tissue removal is provided by a system including a computer controller for successively rapid sequencing of (ii) the photoionization of a beam path through a selected gas environment above the targeted site, and (ii) the creation of a high-intensity electrical field in the beam path to apply energy to the tissue surface for volatilization of a targeted thin surface layer.

The invention advantageously provides a technique for biological material removal that allows for non-contact application of electrical energy to tissue.

The invention advantageously provides a non-contact technique for application of electrical energy to tissue in intense pulses to create an electrochemical decomposition of surface layer portions.

The invention advantageously provides a technique for biological material removal that allows precision of ablation depth by removing a discrete thin layer of material with each pulsed application of energy, thus allowing precise control of volumetric removal by controlling the repetition rate of the pulsed energy applications.

The invention advantageously provides a technique for removal of surface layers of body structure without collateral thermal damage.

The invention advantageously provides a technique for applying energy to a surface that results in an even energy deposition in short pulses.

The invention advantageously provides a technique for removal of surface layers that results in an even surface ablation.

The invention advantageously provides a technique for ablation (material removal) that is generally insensitive to tissue's linear absorption characteristics.

The invention advantageously provides a technique for ablation (material removal) that is generally insensitive to tissue hydration.

The invention advantageously provides a technique for ablation (material removal) that is chromophore independent.

The invention advantageously utilizes an electrical source for energy delivery which is inexpensive in contrast to laser systems.

BRIEF DESCRIPTION OF THE DRAWINGS

FIG. 1A being a plan view of energy deposition wherein the shaded region indicates even energy deposition; FIG. 1B being a partial sectional perspective view wherein the "ideal" even energy deposition creates a uniform depth surface layer removal.

FIG. 2A being a plan view of energy deposition wherein the shaded region indicates uneven energy deposition; FIG. 2B being a sectional view wherein the uneven energy deposition causes lack of uniformity in the depth of ablation.

FIG. 3A being an illustration of a tissue surface with site targeted for UV laser ablation; FIG. 3B being a sectional view of the tissue of FIG. 3A taken along line 3B–3B depicting the first ns of an intense UV laser beam striking the tissue surface; FIG. 3C being similar to FIG. 3B but several ns later depicting an ablation plume or plasma that absorbs energy of the continuing UV laser beam before it reaches the tissue surface; FIG. 3D depicting termination of UV beam delivery after 10 to 100 ns duration and a resultant uneven energy application since the ablation plume absorbed energy from the continuing UV laser beam before it reached the tissue surface; and FIGS. 3E–3F depicting one or more additional pulses of UV laser energy delivery which causes further uneven energy depositions and uneven depths of ablations.

FIG. 5A being an illustration of the working end of the instrument positioned in a selected gas environment over a targeted tissue surface; FIG. 5B depicting irradiation of a path through the selected gas environment to photoionize the gas; FIG. 5C depicting the initiation of an intense electric field the photoionized gas region thereby applying electrical energy to the targeted site; FIG. 5D depicting the electric field an arbitrary ns time interval later when intense electrical field creates a plasma and thereby decomposes a surface layer portion; FIG. 5E depicting a optional step in the method wherein UV energy delivery is terminated while electrical energy delivery is continued to maintain the plasma and apply energy to the tissue; FIG. 5F depicting the tissue removed after termination of energy application, and FIG. 5G depicting a plan view of energy application.

DETAILED DESCRIPTION OF A PREFERRED SYSTEM EMBODIMENT

I. Operational Principles of Non-Contact Electrochemical Decomposition of Thin Surface Layers.

Figure 4:
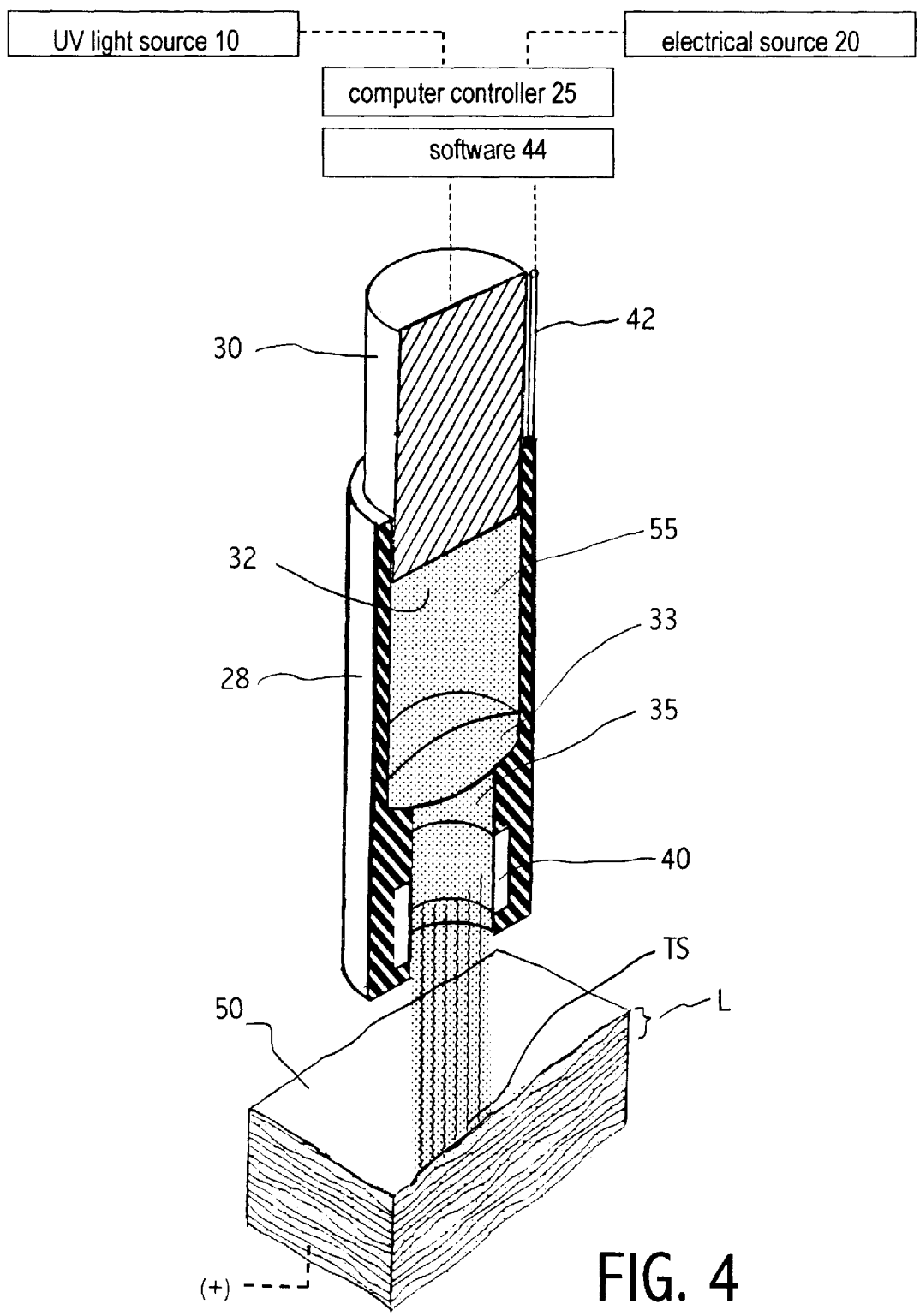
FIG. 4 is a schematic view of the system of the present invention in relation to a targeted tissue surface in phantom view.

Several principles relating to the operation of an exemplary non-contact plasma-mediated electrochemical ablation system 5 (see FIG. 4) for the ratable removal of thin surface layers will be described in the following sections. The principles and system will be described with reference to an exemplary surface of a biological tissue volume, such as a patient's skin. The description and techniques of FIGS. 5A–5E are for exemplary purposes only and are not intended to limit the application of the methods of the invention to a patient's skin. The system may have application in various surface layer ablations or volumetric tissue removals in dermatology and ophthalmology, and may be well suited for LASIK and PRK refractive procedures as will be described in another disclosure. The system 5, which may be described herein as a PASCAL system (photoionization assisted electro-chemical ablation of surface layer), is developed in accordance with the following operational principles, which will be described seriatim. The system 5 of FIG. 4 provides energy a UV energy source 10 and an electrical energy source 20 both controlled by computer controller 25 to provide: (A) ultrafast pulses of energy applied to thin surface layers to create critical density electric field induced microplasma events without transfer of thermal energy to the surface layer, and (B) algorithms for modulating energy pulse duration and repetition rates of energy microplasma events to provide layer-by-layer volumetric material removal of surface layers.

A. Operational Principle: Ultrafast Pulsed Electrical Energy Application for Volatilization of Surface Layer Plasma-Mediated Bulk Removal.

A first objective of the present invention is to provide an ultrafast pulsed application of electrical energy to a targeted site on a surface layer of structure in a patient's body. In this invention, each discrete application of energy (pulse or burst) can be defined by quantity of energy (J) and a duration in which such energy is deposited within the surface layer. A first operational principal of the invention is that, for a given energy quantity in joules, the duration of energy application is less than a threshold electron-to-lattice energy transfer time for the surface layer of the targeted structure. It is postulated that for surface layers of structures here in question, this characteristic energy transfer time is in the range of 10's ps to 10's of ns. Thus, when a high-intensity pulse of energy is absorbed in macromolecules in substantially sub-threshold durations, the mechanism of layer removal can be characterized as a chemical alteration of surface molecules. More specifically, the modality is best described as an eletrochemical-tissue interaction since the energy in the inventive method is applied by means of an intense electrical field. In contrast, if the pulse duration of energy application were at an above-threshold level (e.g., in the ms range) with the energy level being sufficient to cause damage, the mechanisms and characteristics of such an ablation would differ. That is, above-threshold energy delivery would cause damage that is largely thermal in nature which would be characterized by vaporization, melting, denaturation, fracture, etc. In such an above-threshold energy delivery modality, the electron kinetic energy transfer to the material's lattice structure would be dependent on thermal diffusivity, a material property which expresses the ability of heat to diffuse and is equal to the square root of the ratio between heat conductivity and specific heat capacity. The present invention, however, is directed to ultrafast pulses (effectively sub-threshold duration pulses) of electrical energy application that create a critical density plasma from a thin surface layer. More specifically, the intensity of the electrical field (or discharge) and its absorption in the surface layer results in volatilization of macromolecules in the layer thus causing actual ionization of the thin layer and thereby removing bulk of such a surface layer. The energy burst is absorbed non-linearly and produces quasi-free electrons which, in turn, may act as seed electrons to cause an electron avalanche by various ionization processes. (Various ionization processes fall within the scope of the practice of the method, e.g., collisional ionization, multiphoton ionization, and field ionization). These ionization processes lead to irreversible alteration in the surface of the structure as ejecta (gas and bulk material) is ejected from the layer. It is believed that a very high fraction of the applied energy is removed by the high-velocity ejecta. Thus, any instantaneous high temperatures caused by the energy application are removed from the layer by this aspect of the plasma formation processes disclosed herein. It is further believed that mechanical shock waves to the bulk material will be insignificant compared to energy applications at above-threshold levels, as defined above. At the sub-threshold energy duration applications proposed herein in accordance with practice of the method, there will be insufficient time for lattice coupling, thus resulting in insignificant thermal diffusion-induced collateral damage to adjacent tissue layers.

A further desirable consequence of using such ultrafast pulse of energy application for surface layer removal is that the method is relatively insensitive to hydration and density of the targeted surface layer, and is entirely chromophore independent. The drawback to the layer-by-layer plasma-mediated process disclosed herein is that the electrochemical decomposition (or ablation) rate, defined generally as the depth of layer removal per pulsed energy application, is small. That is, each electrical energy application only removes a surface layer portion having a thickness measured in $\mu$m's (microns). It is postulated that layer removal rate will range from about 1 $\mu$m to about 200 $\mu$m within the anticipated energy application parameters (from 0.1 J/cm.$^2$ to 1000 J/cm.$^2$; or 0.1 J to 10 J per pulse). In order to overcome the low rates of material removal per pulse of energy in the typical case that needs substantial volumetric removal, the repetition rate of pulsed energy application must be high. This operational principle of the invention will be described below in Section I(C).

B. Operational Principle: Photoionization of a Beam Path in a Selected Gas Environment Overlying the Targeted Surface Layer The previous Section 1(A) described means for plasma-mediated non-thermal electrochemical decomposition of surface layers of body structure. However, to provide a non-contact energy application method for use in biological surface layer removal processes, it is necessary to define certain operational principles that allow for such (i) a non-contact modality while still allowing (ii) a spatially-controlled application of such energy to a targeted site. The operational principles according to this aspect of the invention relate to means for creating an electrically conductive (partially ionized) beam path in a selected gas environment above the surface layer that is targeted for removal. The ionized path must be maintained for a sufficient time interval to create an intense electrical field therein to thereby cause the plasma-mediated volumetric removal of a surface layer portion.

The present invention utilizes a high-energy photonic (electromagnetic) energy source (e.g., a UV source) to deliver a radiative beam through a selected gas environment between the emitter end of the source and the targeted site to photoionize a path through the gas thereby creating an initial plasma. In such photoionization, the high-energy photonic energy irradiates the neutral gases in the environment and interacts with ionic electrons leading to removal of such electrons from the ions. To photoionize an ion requires a photon energy greater than the binding energy of the electron. As photons increase in energy (wavelength dependent), the cross-section for photoionization of a particular electronic state is zero until at a certain point the cross-section jumps to a finite value, which is termed a photoelectric edge. The method of the invention thus selects a radiation source characterized by photon/wavelength energies beyond the photoelectric edge as it relates to the selected neutral gas environment. For purposes of the disclosure, the term selected gas environment is defined as any ionizable gas that is compatible with biomedical applications, e.g., air, nitrogen, oxygen, $CO_2$, etc. In such photoionization, the departing electrons must exchange virtual photons with the nuclei for the process to occur. Such photoionization, therefore, tends to preferentially remove inner-shell (i.e., K-shell) electrons since these can most readily interact with the nucleus. Due to this effect, this process general leaves highly excited ions. After photoionization by photons of energy, the liberated electrons possess a kinetic energy and successive electron—electron collisions distribute this energy throughout the electron population with such kinetic energy being thermalised into a plasma. This non-equilibrium plasma extends about and along the path of the radiative beam through the gas environment to its incidence on the targeted site. Such an ionized path is highly conductive with respect to an electrical field. It is postulated that the photoionization of the path in the gas environment occurs within a fs or ps time interval upon irradiation with the UV energy described above. The ionization of the path will disappear in a similar brief time interval upon termination of UV energy delivery (absent field ionization effects). (Time intervals of UV light pulses for such photoionization is described below in Section 1(C) which relates to repetition rates). Thus, the photoionized (conductive) path serves as a means for applying an intense electrical energy pulse to the targeted site without the need for an electrode being in direct contact with the targeted site, with the gas, in effect, acting as an electrode (i.e., a gas electrode). The termination of the photoionized path at the surface layer is capable of interfacing an intense electrical field (electrical discharge) with the targeted layer to cause the electrochemical ablation process described in Section I(A).

C. Operational Principle: Controlled High Repetition Rate of Pulsed Energy Applications The above Sections described a novel non-contact electrically induced plasma-mediated ablation process that occurs, per pulse, in a time interval that may range from picoseconds to 100's of ns or even microseconds. In the sequential energy deliveries and plasma formations, only a thin layer of tissue is removed by the electrochemical-tissue interaction. In order to provide functional volumetric removal, the ultrafast pulsed energy event must be repeated at a high rate, and this Section describes operational principles relating to the selection of such a repetition rate. At a theoretical high repetition rate, there will be a high rate of volumetric removal. However, if the repetition rate is too high there may be collateral damage from thermal effects conducted to the surface layer by secondary effects of the thermalized plasma, which could defeat a principal objective of the invention in providing a substantially cold volumetric removal process. While it is postulated that the electrochemical-tissue interaction itself occurs absent a thermal energy transfer, it still is necessary to provide a repetition of ultrafast plasma creation/decay events that will not allow thermal effects to build up in the plasma that, in turn, could be conducted to the surface layer and cause collateral thermal damage.

The operational principle in determining a maximum theoretical repetition rate for pulsed energy applications concerns the relationship between duration of energy absorption effects by the surface layer and the layer's confinement of heat, which thus may result in unwanted collateral thermal damage. The operative construct is the so-called thermal relaxation time of the surface layer, and is defined as the time required for significant cooling of a defined tissue volume of a body structure that has been elevated in temperature. Thermal relaxation is often defined as the time required for an elevated tissue temperature to be reduced by 50 percent. Many processes are involved in such cooling, such as conduction, convection and radiation. Macroscale conduction cooling in body structures probably dominates, but microscale radiational cooling at a very small target site proximate to a plasma may be important. For targeted sites on structure in a patient's body in laser applications, the rule of thumb is that the thermal relaxation time in seconds approximately equals the squared dimension of the targeted site in mm. (For example, a 0.5 $\mu$m size structure ($5\times10^{-4}$ mm.) will substantially cool in about 250 ns ($25\times10^{-8}$ seconds)). In the case of the inventive method disclosed herein, the fact that the targeted surface layer is exposed to a gas environment is advantageous in that any heat will rapidly dissipate into that gas environment.

In accordance with practicing the principles of the method, it is postulated that ultrafast pulses of energy will be absorbed in the range of 100's of ps to 100's of ns. It is further postulated that repetition rates in the range of from about 10 Hz to about 1000 Hz are possible without exceeding the relaxation time of the surface layer. (At this time, the repetition rates are theoretical and are to be explored with experiments). Thus, surface layer removal rates could be as high as 1 mm./s while maintaining the desired minimal collateral damage characteristics of the plasma-mediated decomposition or ablation.

II. Construction of Exemplary System for Photoionization Enabled Electrochemical Decomposition of Layers Referring to FIG. 4, an exemplary Type "A" embodiment of energy application system 5 is shown with an instrument assembly indicated schematically at 26 that carries a working end 28 that emits UV wavelengths, and electrical energy, therefrom toward a targeted tissue surface. In this disclosure, the working end 28 is adapted for positioning above or spaced apart from the targeted site to accomplish the non-contact method of plasma-mediated electrochemical decomposition. The terms decomposition and ablation are used interchangeably herein to characterize the surface layer removal process, and other words descriptive of the process may be used in this disclosure, such as, tissue breakdown, disintegration, obliteration, removal, or volumetric removal to describe and define the plasma-mediated process that causes exposed layers of a structure in, or on, a body to be altered, broken down, destroyed, damaged, or fragmented and removed or ejected from the surface layer. The term structure of a patient's body as used herein is intended to be inclusive of any exposed surface layer of a patient's body, and principally in intended to identify layers of a patient's skin, or surface cornea layers or exposed intrastromal layers.

The working end 32 may be carried at the distal end of a hand-held probe, or more typically may be coupled to any type of assembly for stabilization or robotic manipulation and fixation relative to a stabilized targeted tissue surface. As can be seen in FIG. 4, the working end 28 carries within a central light-carrying channel 30 which typically is an optical fiber channel but also may be any suitable form of waveguide, light tube, articulated arm with mirrors, or an open beam delivery system including coated reflectors and lenses to focus the radiative beam. The working end 28 has a central passageway 32 therein that carries a lens element indicated at 33 which comprises the distalmost termination of the UV light delivery system. The lens element 33 may be any suitable power (or lack thereof) and fall within the scope of the invention and is adapted to project the radiative beam to the targeted site with a selected coverage at the site. It should be appreciated that the UV source indicated at 10 includes any components typical of a light source plus a delivery system, which typically includes, but is not limited to, a coherent or non-coherent light source together with fiber optics, lenses, mirrors, prisms, filters, splitters, combiners, shapers, shutters, power attenuators and other arrangements operatively connected between the actual light source and the emission of a light beam through the lens 33. FIG. 4 shows that a free chamber portion 35 of central passageway 32 is provided distal from the lens 33 that is contained by wall cylindrical wall portion 36 of non-conductive material for the projection of UV light therethrough. The length of chamber portion 35 may range from about 0.5 mm. to 25.0 or more and is adapted to contain and circumferentially contact the UV beam path and provide a relatively broad interface between the photoionized gas within the chamber and the conductive electrode arrangement indicated at 40. The diameter of the chamber may be from about 0.1 mm. to 20.0 mm. or more depending on the application.

The computer controller 25 interfaces with the UV light source 10, and controls the activation of the source, as well as its pulse repetition rate in response to control signals that are provided by the system operator. Any sort of on-off switch (foot pedal or hand switch, not shown) is connected to controller 25 and provides activation signals in response to switch actuation. The pulse repetition rate may be set by the operator by a form of rheostat control connected to controller 25 which increases or decreases the repetition rate in response to the operator selection. The light source 10 may be an excimer laser, such as an Ultralase system by NEXEX, Inc., 6301 N.W. $5^{th}$ Way, Ft. Lauderdale, Fla. It also should be appreciated that any non-coherent high-intensity UV source may be suitable for delivering energy along the light-carrying channel 30, for example a conventional discharge lamp as is known in the art together with optional filters, combiners, and associated optics to perform the method of photoionization aspect of the method described above. The UV energy radiated from source 10 is pulsed by computer controller 25 which is capable of controlling the delivery of light pulses at pulse durations ranging from about 100 ps to tens of ms with a repetition rate ranging from about 1 Hz to 1000 Hz.

Referring again FIG. 4, the electrical source indicated at 20 comprises the energy delivery means for performing the electrochemical tissue decomposition. An intense electrical field is developed in the photoionized gas path by means of electrical discharge delivered from source 10 via current-carrying wire or lead 42 to an exemplary conductive electrode 40 that has an annular configuration around the surface of chamber 35. The electrode 40 may be a single unitary element or a plurality of elements all connected to electrical leads 42 hand to the same negative (−) source polarity. In accordance with the practice of the invention, the electrode 40 may have an active surface with a particular surface geometry shape that is adapted to enhance the intensity of the electric field and the current density at the time of each pulsed energy delivery. For this reason, such surface geometry preferably may include at least one projecting portion or varied sharp edge portions at the active surface. The preferred surface geometry comprises an electrode in a 360° band with a plurality of micro-scale sharp elements that may be characterized simply as surface roughness on the active surface of the electrode. Such a surface may be provided by any suitable chemical, electrochemical or abrasive method to create micro-edges or asperities on the active surface portion to thus enhance the high electric field intensities at the active electrode surface.

As shown in the block diagram portion of FIG. 4, the electrical source 20 may be any suitable electrical energy source as is known in the art than is capable of delivering high intensity electrical current, for example in the range of 10 to 2000 volts. The electrical source 20 preferably delivers any selected high frequency voltage that is selected from a range, or modulated within a range, to generate average power levels ranging from a few milliwatts to hundreds of watts depending on the targeted surface layer and the desired the rate of removal. The controller 25 that interfaces with the electrical source 20 allows the operator to select the voltage level according to the specific requirements of surface layer removal procedure. It is postulated that the voltage applied between the active electrode and the surface layer and return electrode will be in the range from about 50 volts to 2000 volts. The electrical source 20 is coupled to computer controller 25 to control the timing of energy delivery in relation to the timing of the photoionization step, and also may be programmed with suitable software 44 to allow independent modulation of parameters of electrical energy delivery, including: (i) voltage, current and peak electrical power per time interval; (ii) the length of a time interval of current delivery; (iii) the repetition rate of current delivery intervals, and (vi) the profile of energy delivery within each current delivery time interval.

Figure 5A:
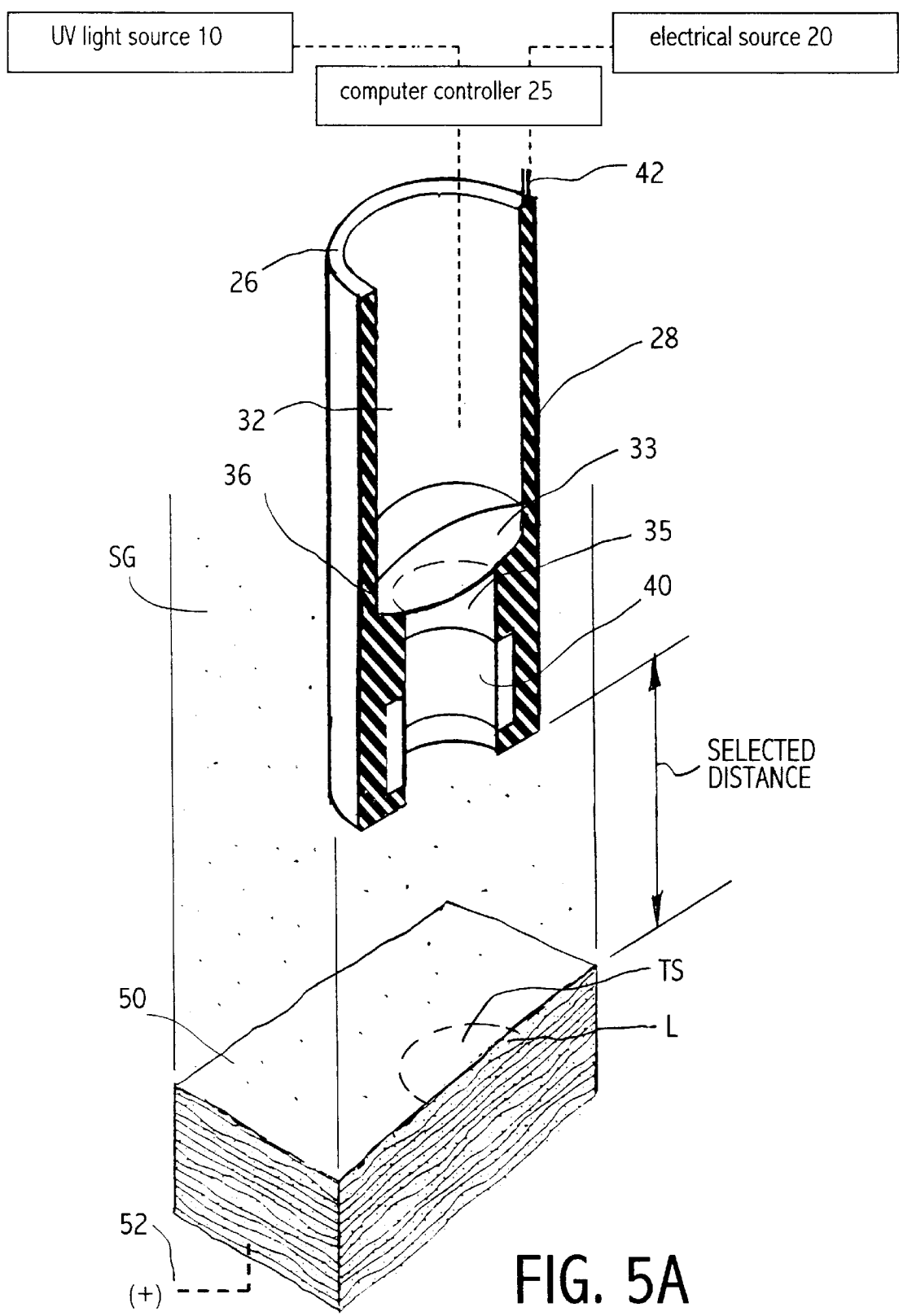
FIGS. 5A–5G are graphic representations of the sequence of steps that comprise the method of practicing the principles of the invention for removing surface layer portions of body tissue.

III. Method of Non-Contact Photoionization Enabled Electrochemical Decomposition of Surface Layers In practicing the method of the invention as shown in FIGS. 5A–5E, an exemplary tissue volume 50 is shown with surface layer L. A targeted site indicated at TS is shown which is to be removed or ablated. FIG. 5A shows that the tissue volume 50 is coupled to a positive (+) electrode 52 (ground pad) as is known in the art.

Referring to FIG. 5A, a schematic view of working end 28 is shown positioned a suitable distance from the targeted layer L for example form about 2.0 mm. to 100.0 mm., and more preferably from about 50.0 mm to 20.0 mm. the region between the lens 32 and the targeted site TS comprises a selected gas environment SG, which in this descriptive example of the method may be presumed to be ordinary air.

Figure 5B:
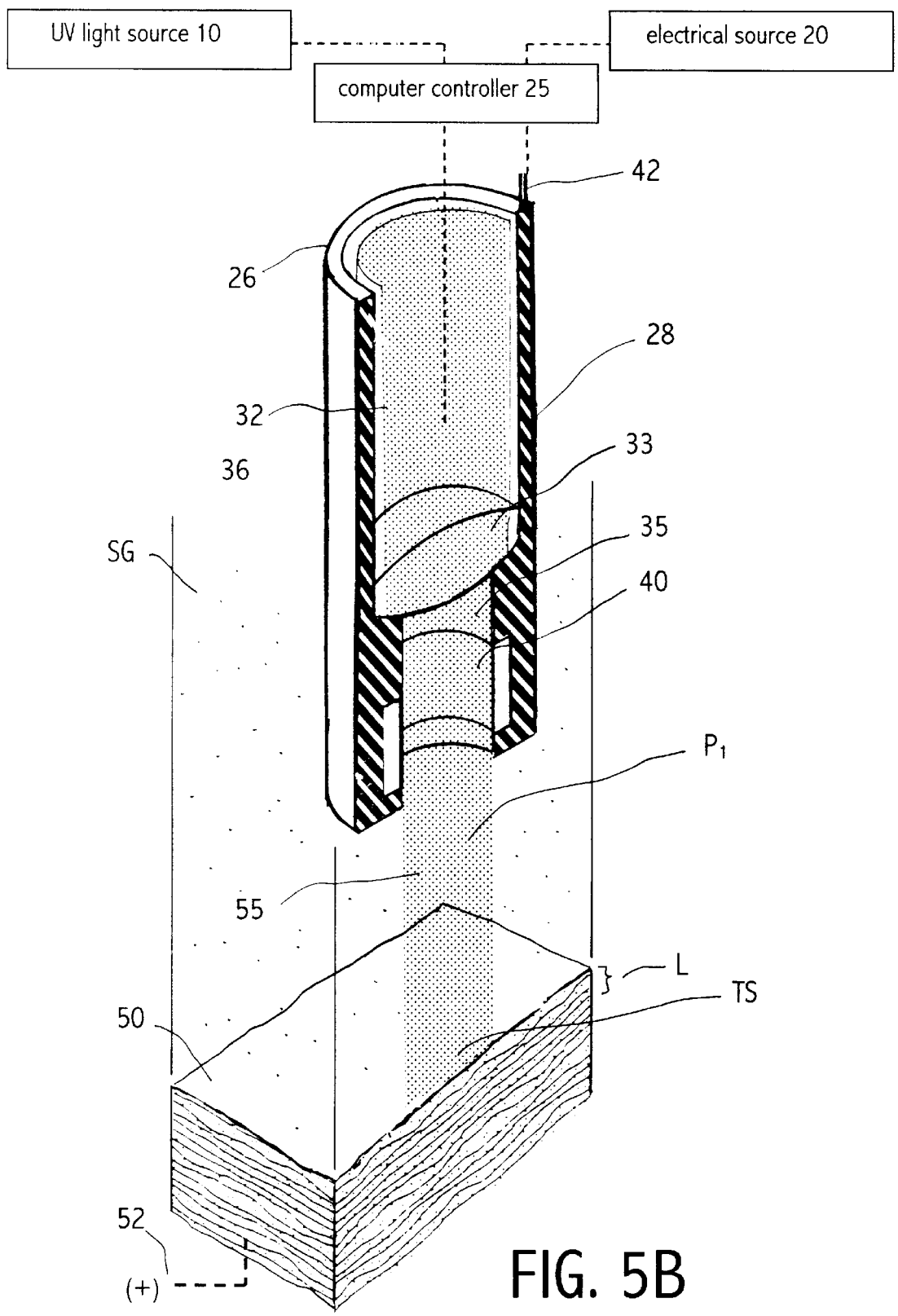

Turning to FIG. 5B, the controller 25 actuates at time $T_{PI}$ (time of photoionization initiation) the UV source 10 for a pre-selected time interval to thereby irradiate a path through the selected gas SG with UV energy via beam 55 that is carried via light channel 30. FIG. 5B hence depicts the step of photoionizing the selected gas SG to create a conductive plasma (photoionized gas) indicated at $P_1$ that will remain in such a non-equilibrium state for the duration of UV energy delivery (in the absence of field ionization effects). The UV light is delivered in substantially low intensities for photoionization purposes, and such intensities will not volatilize and remove tissue.

Figure 5C:
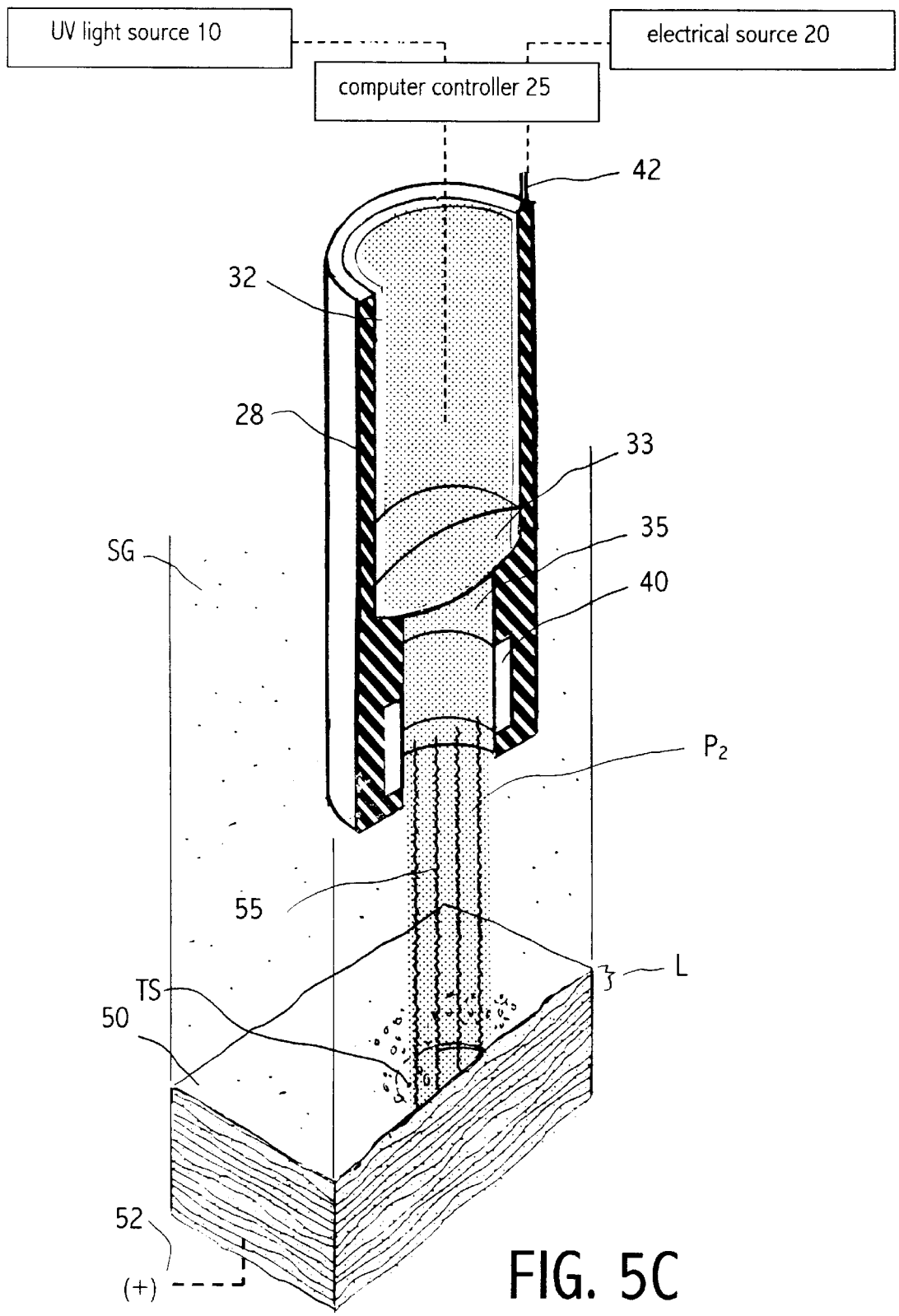

Now turning to FIG. 5C, the controller 25 actuates at time $T_{EFI}$ (time of electric field initiation) the electrical source 10 to deliver a high-voltage electrical energy pulse to the active electrode surface 40 which creates an intense electrical field in the photoionized gas (plasma $P_1$). In turn, the intense electrical field applies energy to the targeted site TS which spatially comprises the incidence of beam 55 on surface layer L before such ionized gas expands in all directions. FIG. 5C at time $T_{EDI}$ thus depicts the initial ns of electrical energy delivery to the targeted site and further depicts the volatilization and ionization of layer L resulting in electrochemical decomposition of layer portions and bulk removal. The time of electric field initiation ($T_{EFI}$) preferably is timed to occur substantially at the instant of initiation of photoionization of ($T_{PI}$) or it may occur at any fractional second time interval later. FIG. 6A shows an exemplary timeline for the sequencing of energy deliveries, and plasma formation and decay events that correspond to FIGS. 5A–5F as shown.

Figure 1A:
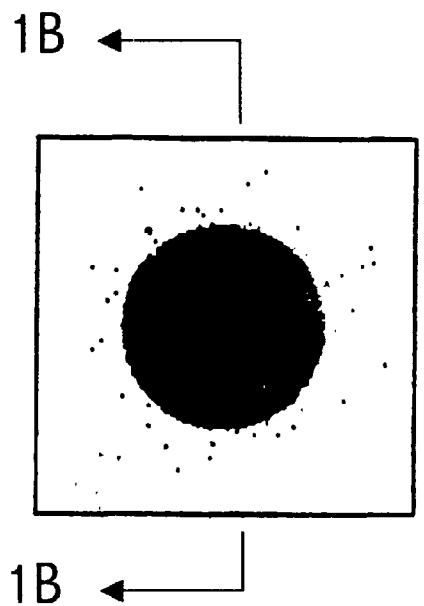
FIGS. 1A–1B are schematic views an "ideal" laser beam's application of energy to a tissue surface to ablate surface layers.
Figure 1B:
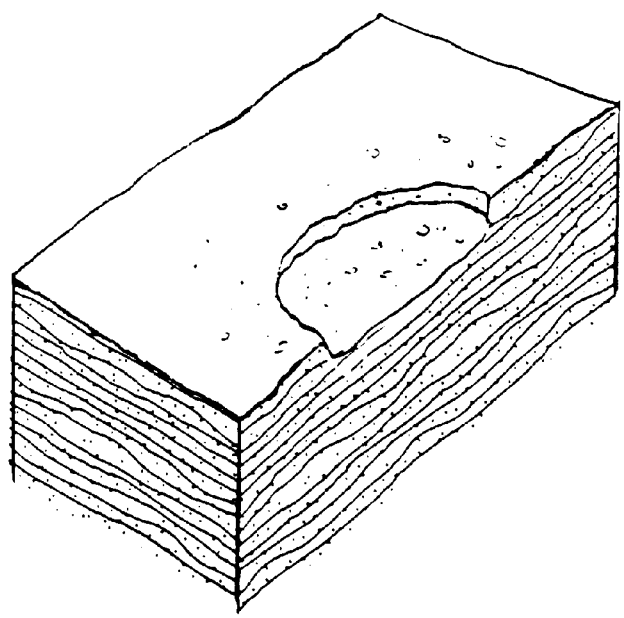
Figure 2A:
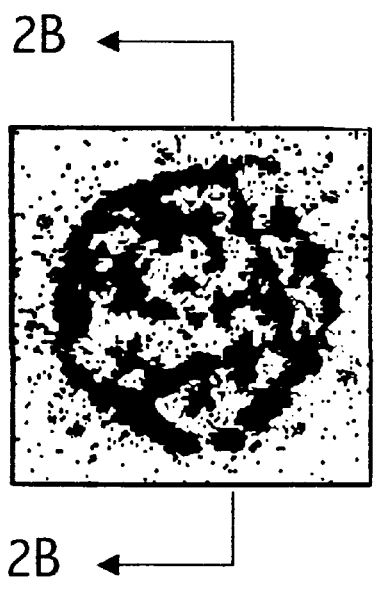
FIGS. 2A–2B are schematic views of hypothetical prior art laser energy application with UV radiation to ablate surface layers of tissue.
Figure 2B:
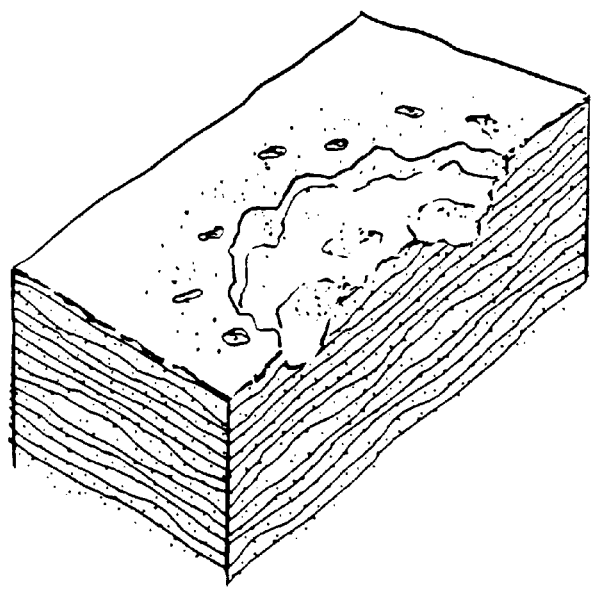
Figure 3A:
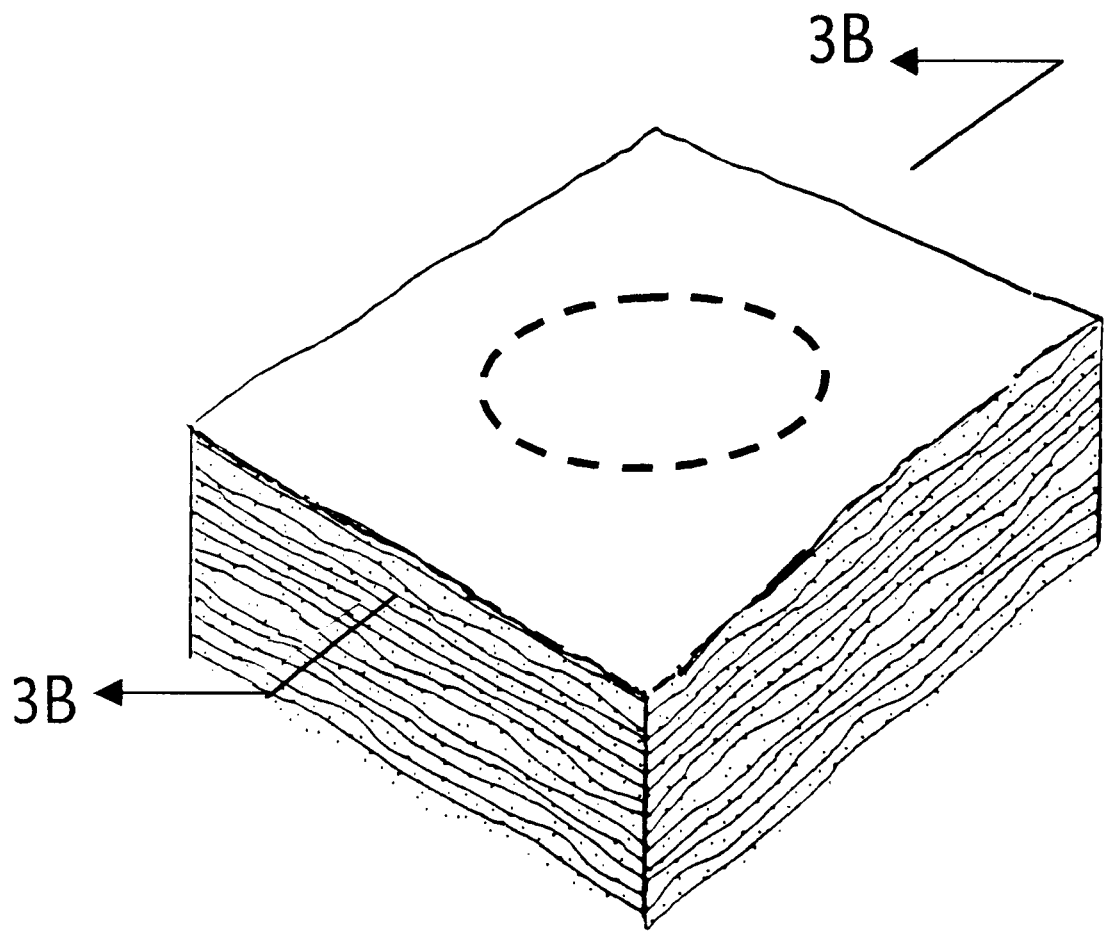
FIGS. 3A–3F are a sequence of illustrations of prior art UV laser energy applications that explain reasons for potentially uneven energy depositions.
Figure 3B:
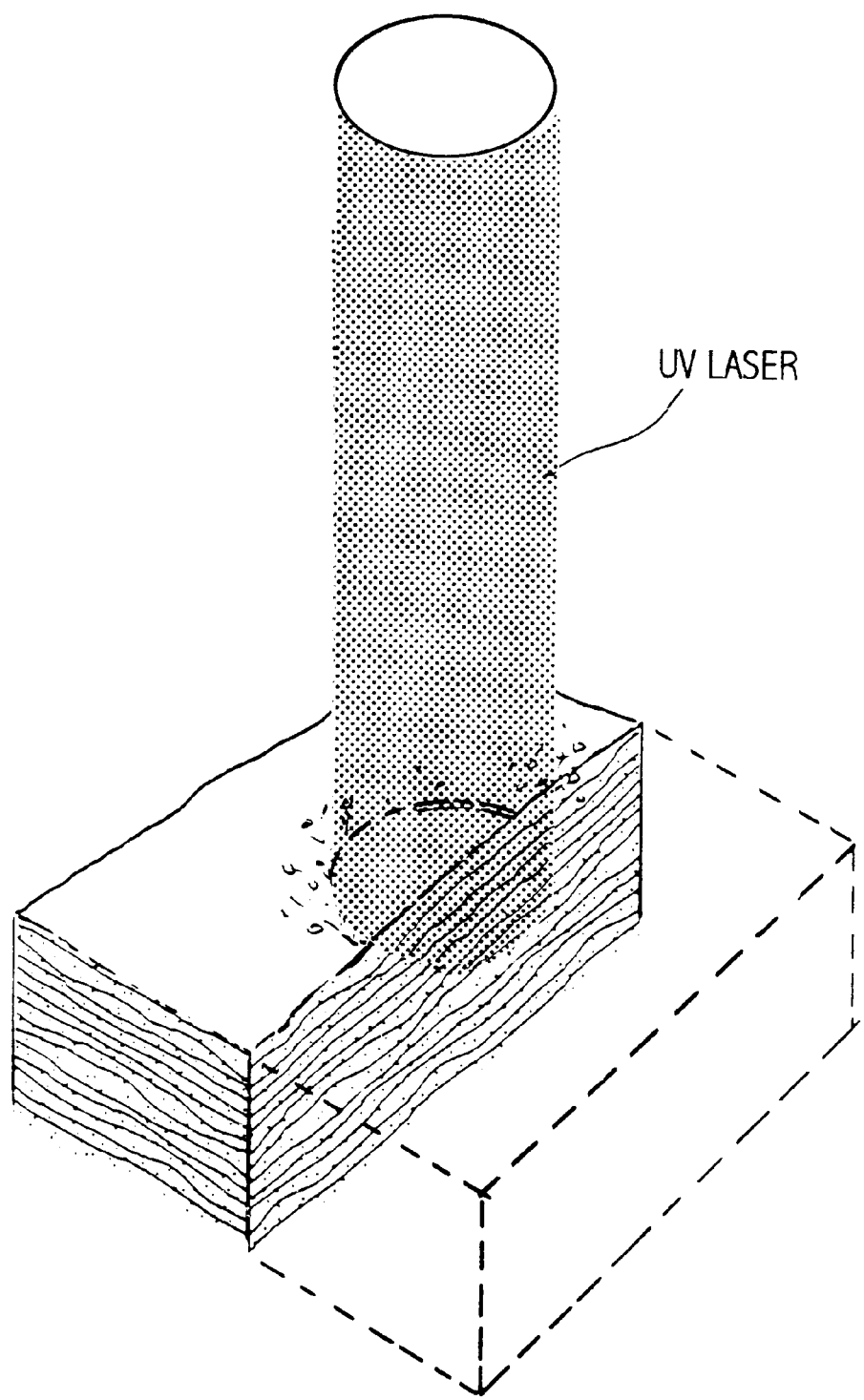
Figure 3C:
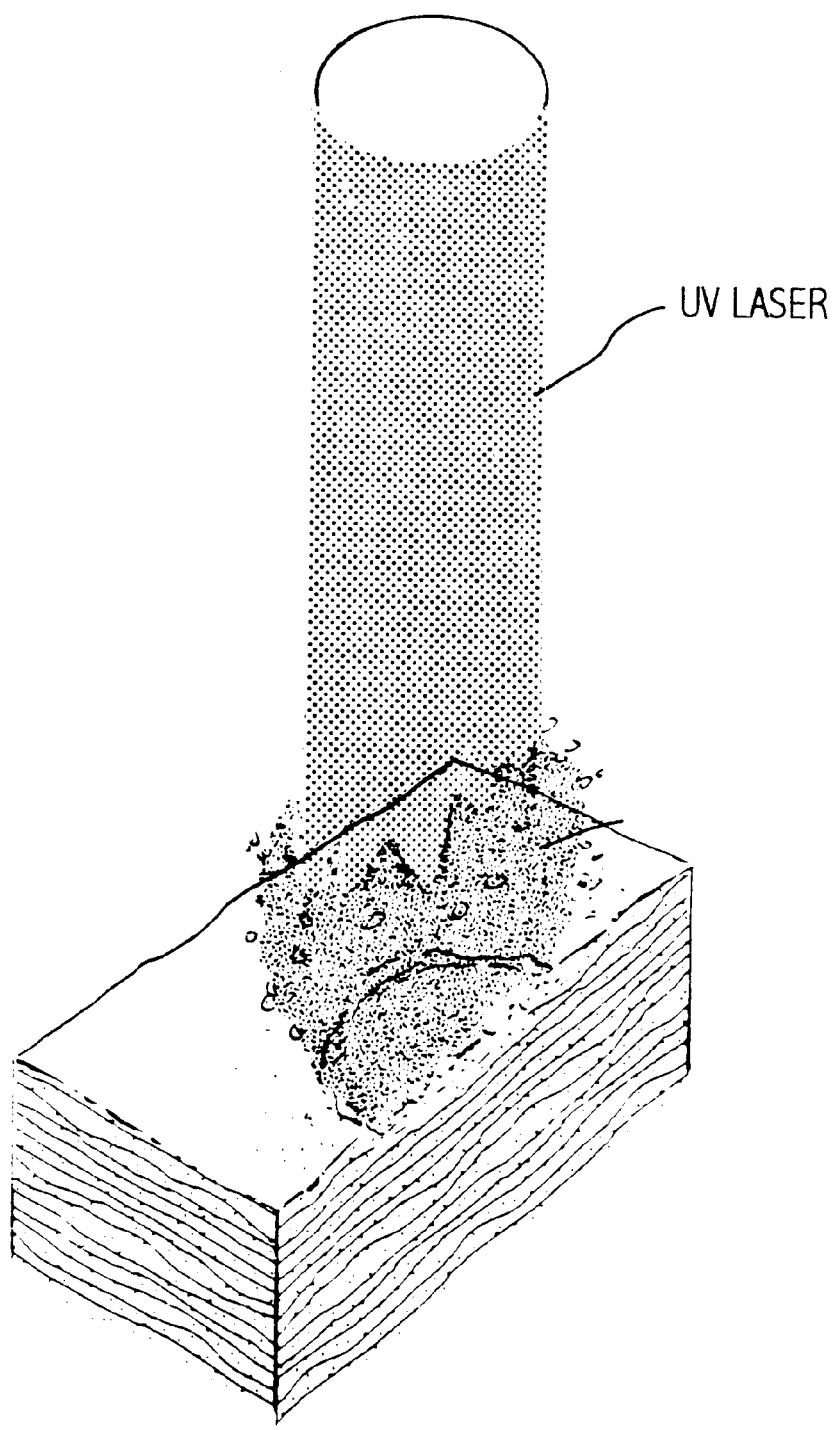
Figure 3D:
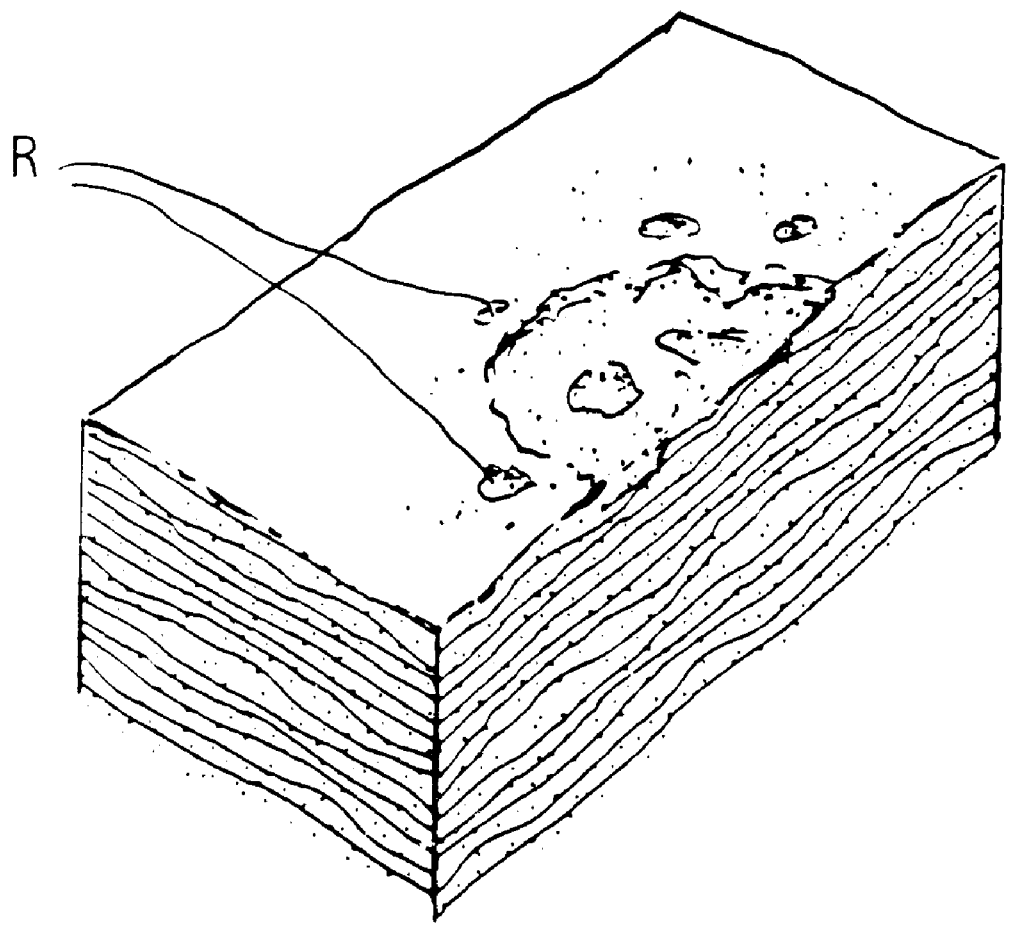
Figure 3E:
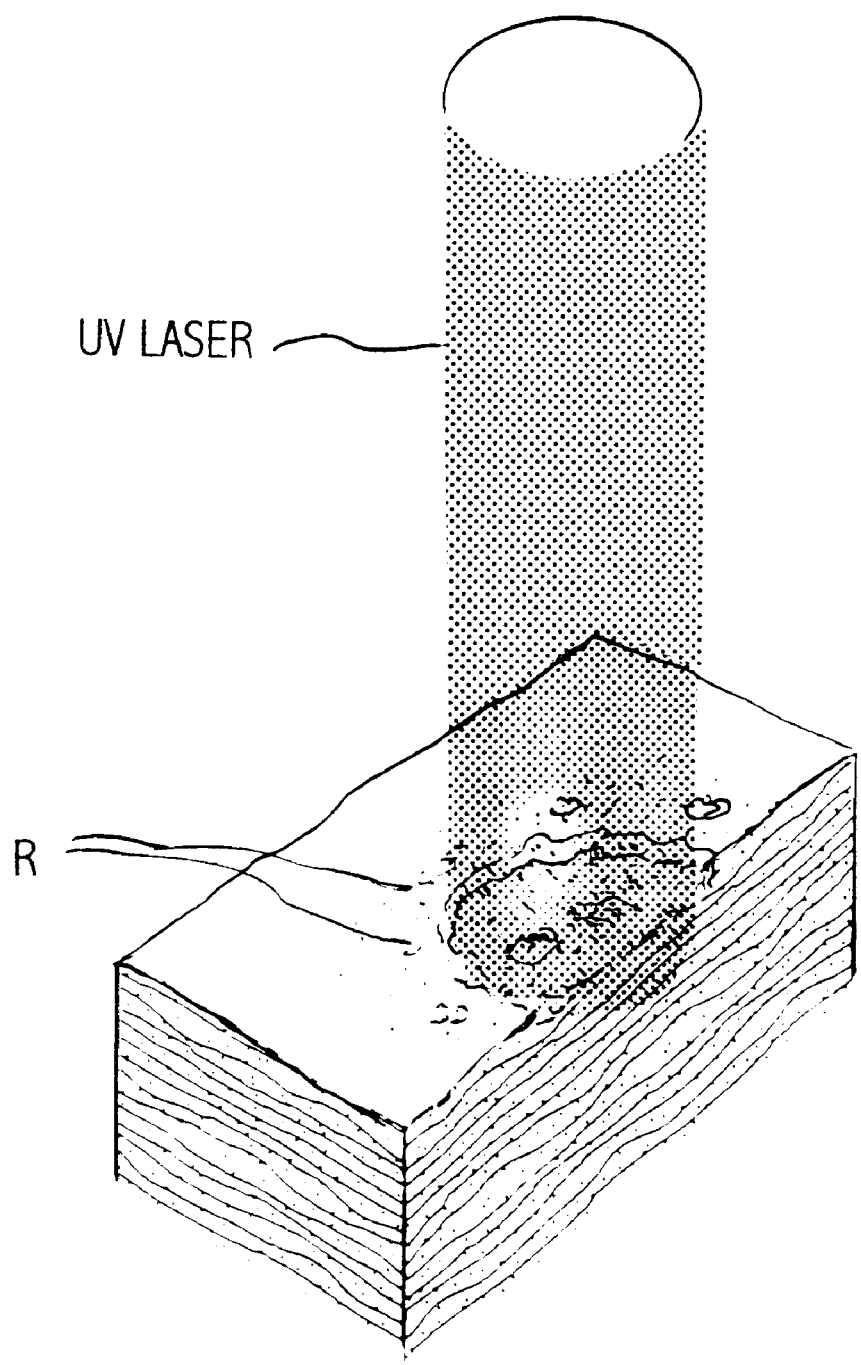
Figure 3F:
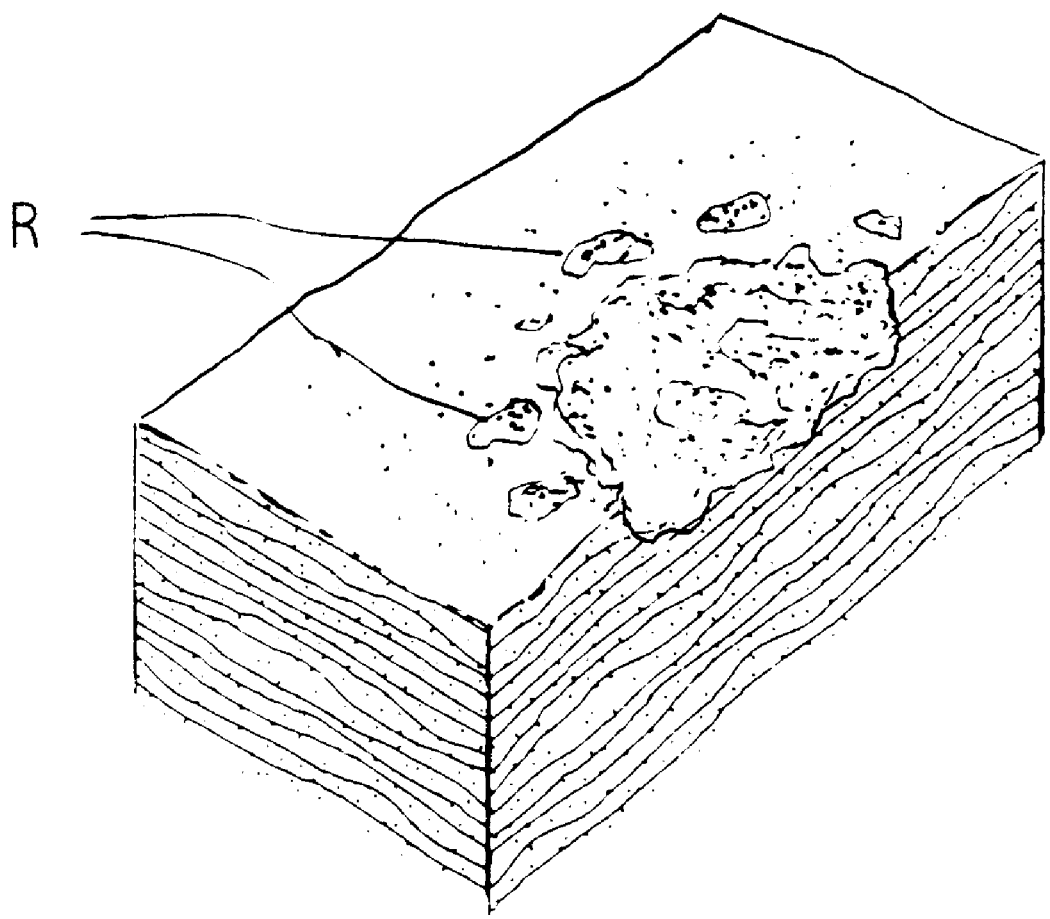
Figure 5D:
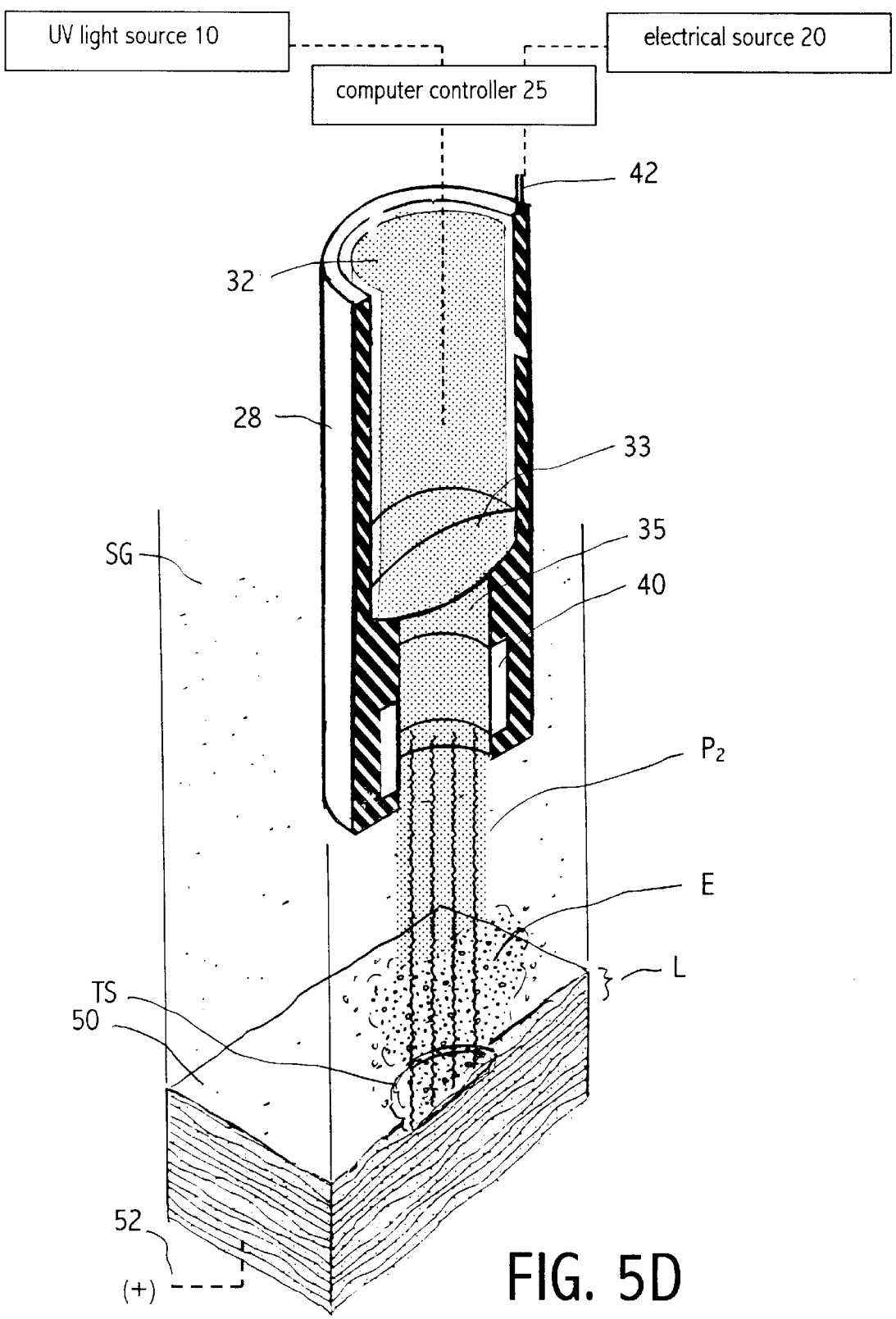
Figure 6A:
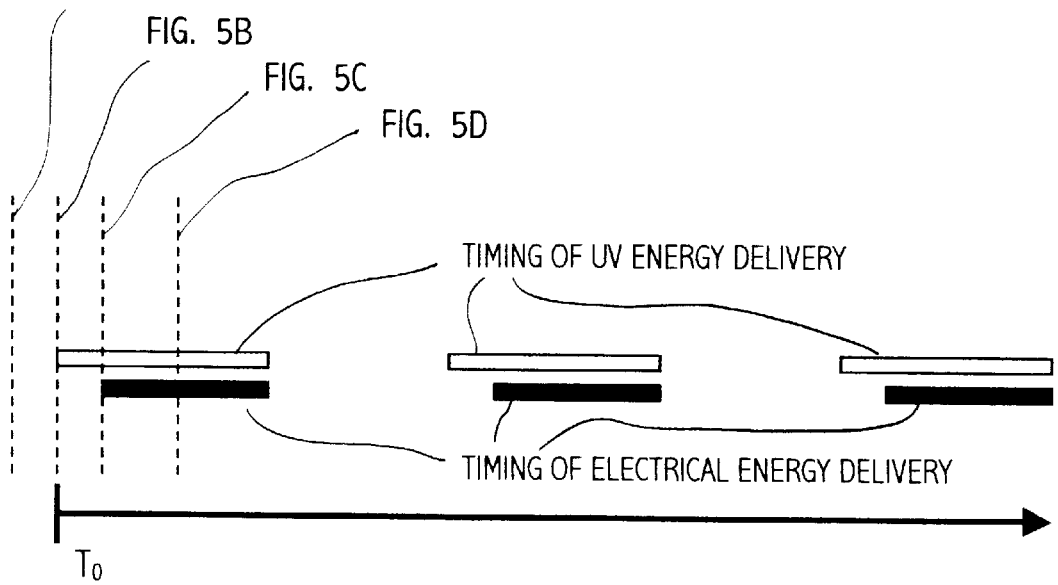
FIG. 6A is a timeline of (i) UV energy delivery to photoionize a path in the selected gas and (ii) electrical energy delivery to remove a surface layer of tissue.

FIG. 5D represents a novel aspect of the method of the invention in the application of an intense energy pulse to the targeted site TS at time $T_{EPI+1\ a.u.}$ (time of electrical field initiation+one arbitrary unit (a.u.) of time). At an arbitrary unit of time ranging from several 10's of ns to a 100's of ns after the initiation of electrical energy delivery, a significant plume of plasma indicated at $P_2$ is created from the surface layer L as ejecta E in which is ejected into a cloud above the targeted site TS. From practically the instant of initiation of electrical energy delivery, such plasma plume $P_2$ will block UV penetration. At that time however, the electrical field in the plasma $P_2$ will maintain the ionization to allow electrical energy to flow through the plasma $P_2$ to the surface layer unabated. In other words, the plasma $P_2$ will cause no interference with electrical energy flow (although such plasma $P_2$ would block excimer laser (UV penetration) in the prior art modality of UV energy application shown in FIG. 3C). Thus, a significant advantage is that an energy delivery interval of longer duration is possible with the present invention than is possible with excimer laser ablation. Thus, material removal rates can be higher per pulse of energy with the application of electrical energy of the present invention than would be the case with excimer laser energy delivery.

Figure 5E:
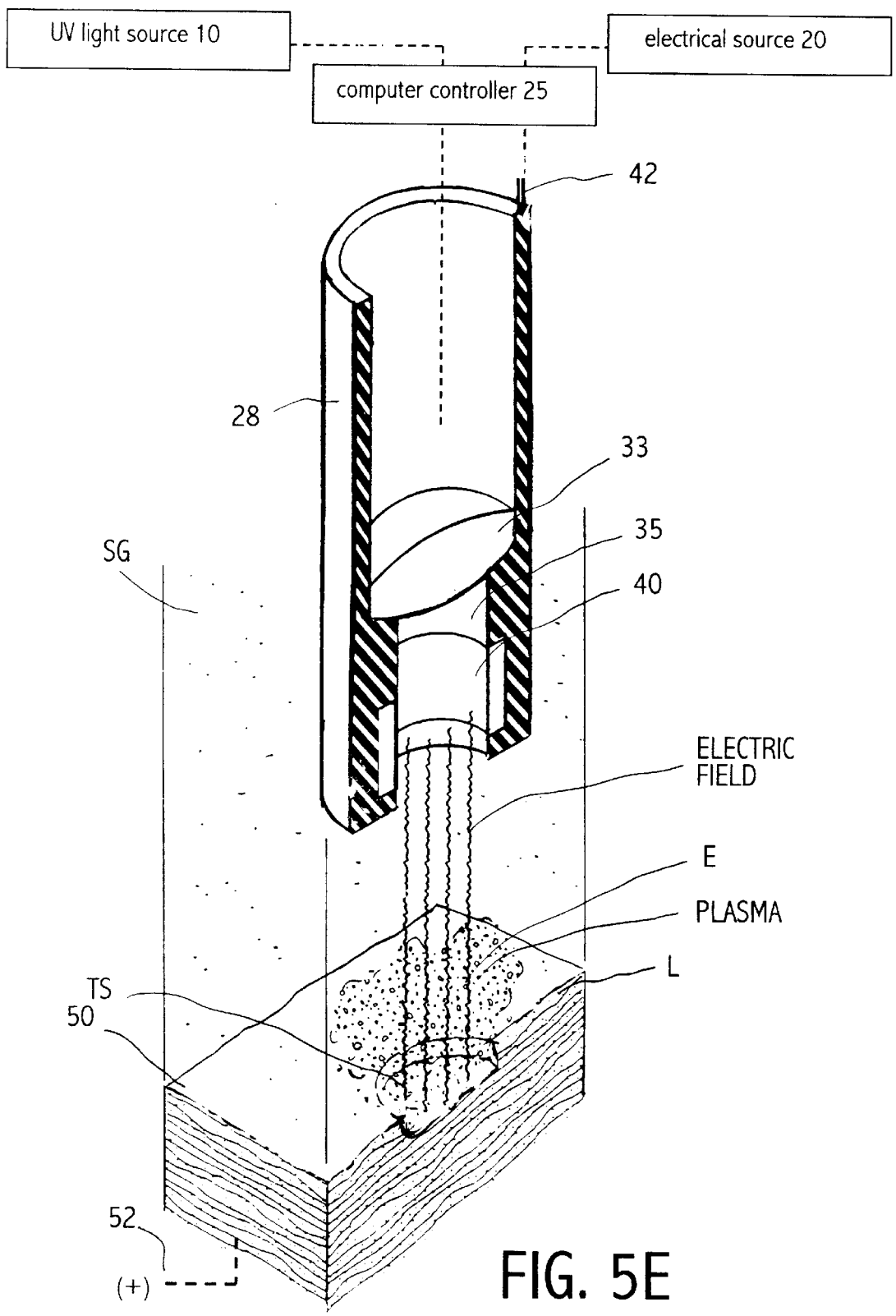
Figure 6B:
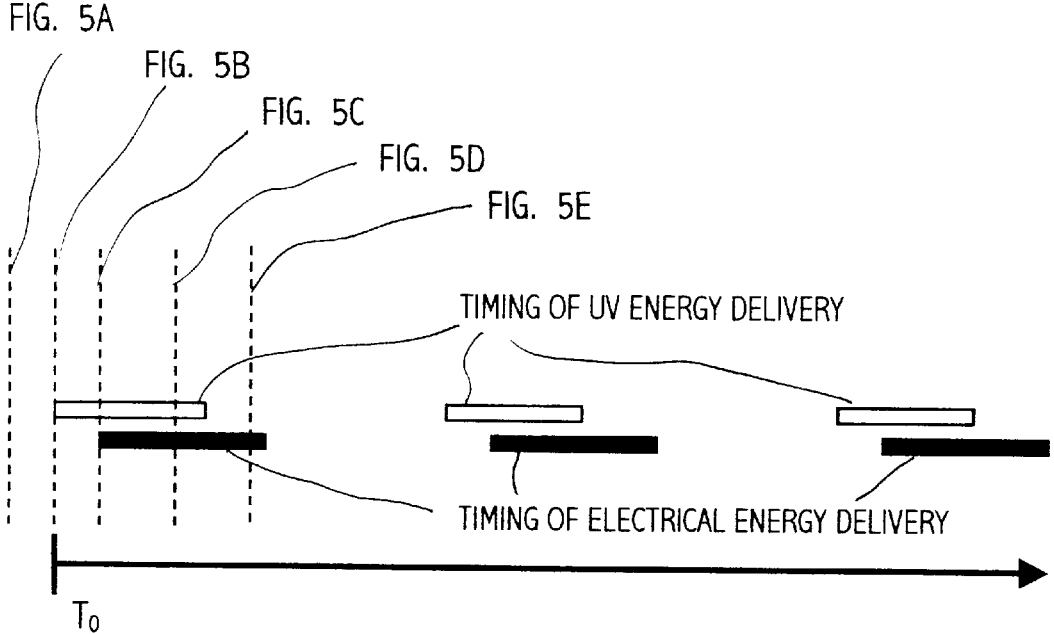
FIG. 6B is an alternative timeline of (i) UV energy delivery and (ii) electrical energy delivery that differs from the timeline of FIG. 6A.

FIG. 5E represents another (optional) step in the method of the invention. Normally, the time of photoionization termination ($T_{PT}$) at which UV energy delivery is terminated is coterminous with time of electrical field termination (or $T_{EFT}$) as shown in FIG. 6A. However, FIG. 5E shows surface layer L subsequent to a time $T_{PT}$ (time of photoionization termination) in which the UV energy delivery is no longer applied but electrical energy delivery continues. In other words, for a period of 10's of ns to 100's of ns, the electric field may be maintained in the selected gas SG by the electrical energy itself maintaining the ionization process (in effect, field ionization instead of photoionization) to allow electrical energy to be conducted by the plasma to the targeted site TS. FIG. 6B shows an optional energy pulse timeline that corresponds to illustration of FIG. 5E.

Figure 5F:
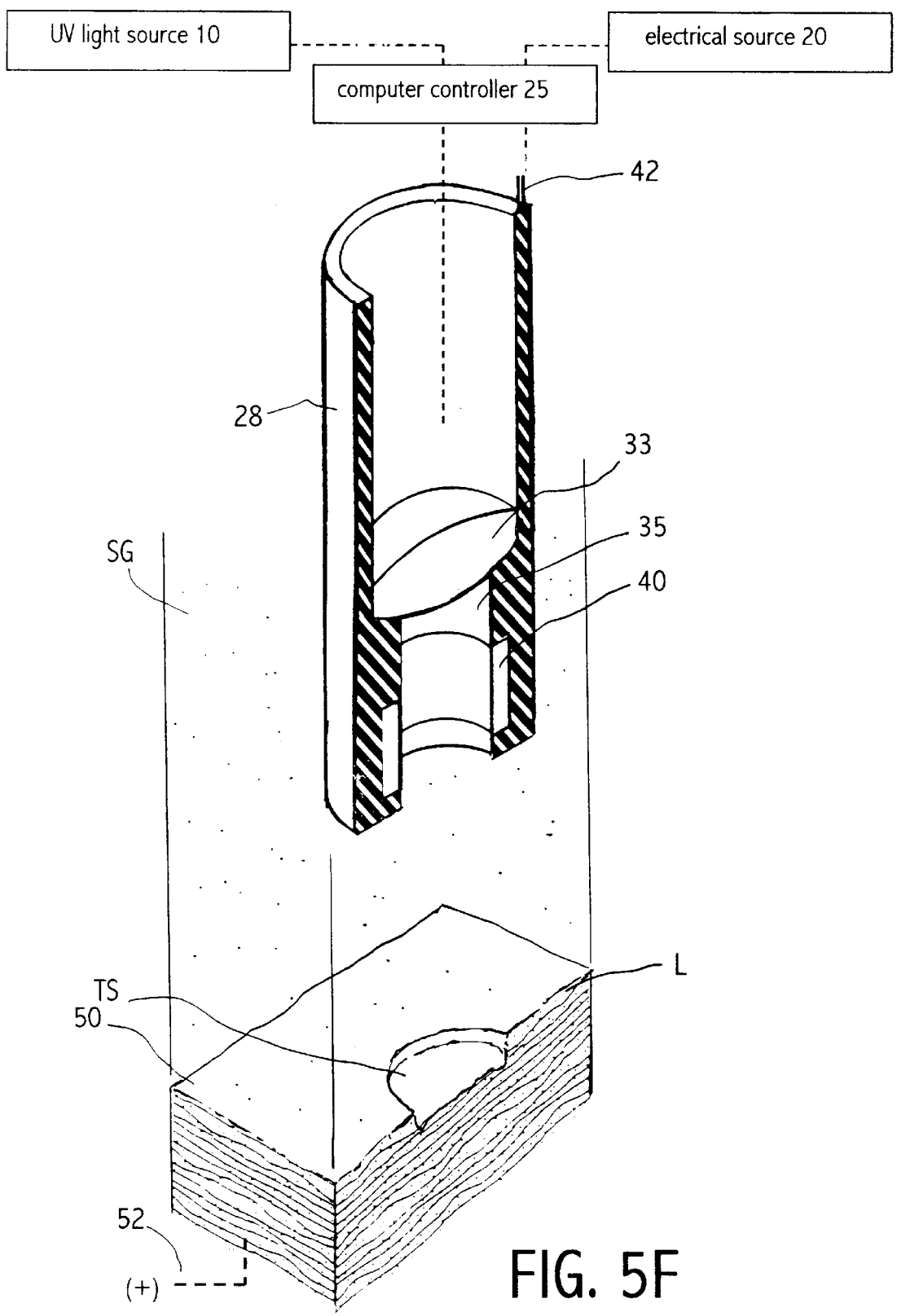
Figure 5G:
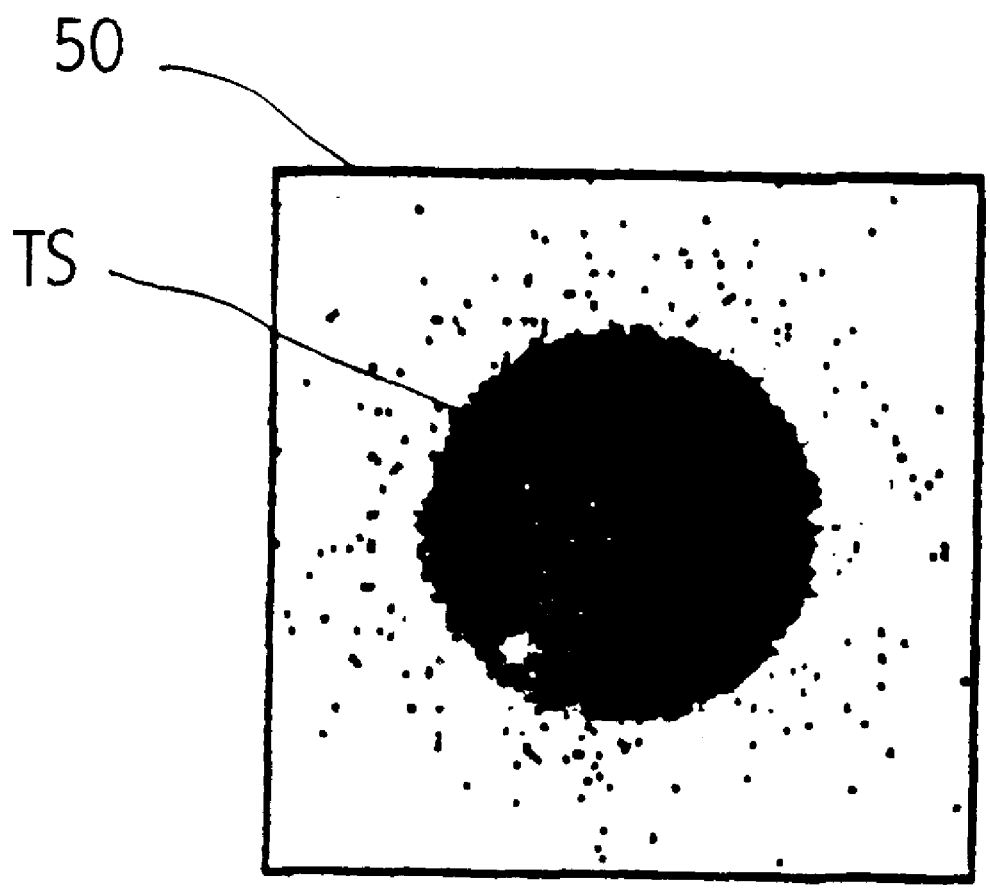

In FIG. 5F, the results of volatilization of surface layer L are depicted after the termination of electrical energy application. Material is removed from the layer L by the application of an energy quantity with molecular decomposition resulting in ejecta E that is ejected to form plasma $P_2$, wherein the ejecta is essentially gases and bulk material detritus. In a brief time interval subsequent following termination of energy delivery, the plasma will decay. Thereafter a repetition of the energy pulses (or plasma-mediated material removal events) occurs as the controller 25 repeats the sequence of events in accordance with FIGS. 5A–5F wherein the time between the initiation of energy pulses defines a repetition rate (see FIGS. 6A–6B). FIG. 5G depicts a plan view of the electrical energy deposition on the targeted site TS of FIG. 5F wherein it is postulated that molecular and surface volatilization will be very uniform in depth for (i) energy delivery pulse widths extending to hundreds of ns, and (ii) over a surface area ranging from about 0.25 mm.$^2$ up to 5.0 mm.$^2$ While the non-contact plasma-mediated electrochemical decomposition method of the present invention has been described in connection with an exemplary exposed tissue surface, it will be clear to those having skill in the art that the system 5 has operational characteristics that may be suitable for a range of material removal procedures in, or on, structure of a patient's body. The system and method of the invention are suitable in particular for dermatologic procedures and ophthalmologic procedures such as corneal surface ablation. In the field of skin resurfacing, the characteristics of the system disclosed herein may prove suitable for application in cosmetic procedures to sculpt or resurface a patient's skin as well as in the field of burn debridement. From the foregoing, it can be seen that the method and system of the present invention provide means for the precision removal of tissue layer by layer with pulsed applications of electrical energy in the ps or ns range such that there is insignificant transfer of energy to the target material lattice in the form of thermal energy. As application of energy is compressed in time, varied ionization processes combine in forming a plasma that ablates material form the targeted surface layer. When operating in an ultrafast electrical energy application regime, energy deposition is localized in a thin layer and the effects decay before significant thermal conduction and hydrodynamic motion can occur in the material lattice, thus preventing collateral thermal damage. Those skilled in the art will appreciate that the exemplary embodiments and descriptions thereof are merely illustrative of the invention as a whole, and that variations in means of ionizing the neutral gas, in the duration of pulses in energy delivery, in the pulse repetition rate, and in the voltage applied to create the electric field may be made within the spirit and scope of the invention.

Accordingly, the present invention is not limited to the specific embodiments described herein, but rather is defined by the scope of the appended claims. Specific features of the invention may be shown in some figures and not in others, and this is for convenience only and any feature may be combined with another in accordance with the invention. While the principles of the invention have been made clear in the exemplary embodiments, it will be obvious to those skilled in the art that modifications of the structure, arrangement, proportions, elements, and materials may be utilized in the practice of the invention, and otherwise, which are particularly adapted to specific environments and operative requirements without departing from the principles of the invention. The appended claims are intended to cover and embrace any and all such modifications, with the limits only of the true preview, spirit and scope of the invention.

What is claimed is:

1. A method for applying energy to a targeted site on a biological tissue mass, comprising the steps of:
    (a) irradiating a beam path from an energy source through a selected gas environment to said targeted site with electromagnetic energy having a wavelength ranging between about 10 nm to 300 nm, the electromagnetic energy having a selected fluence suitable for photoionizing the selected gas in beam path;

(b) delivering an intense pulse of electrical energy for a selected time interval to said photoionized path in the selected gas environment wherein the electrical energy is thereby applied to said targeted site on said biological tissue means.

2. The method of claim 1 wherein the electrical energy of step (b) is of an intensity that causes volatilization of molecules in surface layers of the targeted site to thereby create a plasma, wherein such plasma creation process causes volumetric removal of surface layer portions.

3. The method of claim 1, further comprising the step of repeating steps (a) and (b) at a sustained repetition rate thereby removing surface portions of the site layer by layer.

4. The method of claim 1, wherein the step (b) includes creating an electrical field by passing an electrical current in the ionized gas volume having a voltage that ranges between about 10 volts and 2000 volts.

5. The method of claim 1, wherein a repetition of steps (a) and (b) define a pulse repetition rate, and further including the step of selecting a pulse repetition rate wherein surface layer portions are removed with substantially no transfer of thermal energy into layers portions below or adjacent to the targeted site and with substantially no collateral damage thereto.

6. The method of claim 5, wherein the pulse repetition rate ranges between about 1 Hz and 1000 Hz.

7. The method of claim 1, wherein the surface layer of the site has a characteristic thermal relaxation time and the plasma-to-surface layer energy transfer time per pulse of plasma is less than said characteristic thermal relaxation time such that negligible thermal energy is transferred into the surface layer.

8. The method of claim 1, wherein in step (b), each plasma pulse applies energy in the range of about 0.01 J to about 10 J.

9. The method of claim 1, wherein in step (b), each plasma pulse applies energy to the structure in the range of from about 0.1 $J/cm^2$ to about 1000 $J/cm^2$.

10. The method of claim 1, wherein each steps (a) and (b) define a material removal rate in the range of from about 0.1 $\mu$m to about 200 $\mu$m per plasma pulse.

11. A method for removal of a surface layer at a selected site on a biological tissue mass, comprising the steps of:

projecting a radiative beam from an energy source through a selected gas environment to the selected site, said radiative beam having a wavelength within the electromagnetic spectrum ranging between about 10 nm to 300 nm thereby photoionizing the selected gas in path of the beam; and creating an intense electrical field for a selected time interval in the photoionized path, the field intensity sufficient to cause volatilization of molecules in surface layers of the targeted site thereby creating a plasma, wherein such plasma creation process causes volumetric removal of surface layer portions at the selected site.

* * * * *